(12) United States Patent
Wilford

(10) Patent No.: US 8,147,772 B2
(45) Date of Patent: Apr. 3, 2012

(54) ANIMAL WASTE PROCESSING

(76) Inventor: Philip Graham Wilford, Langley (CA)

( * ) Notice: Subject to any disclaimer, the term of this patent is extended or adjusted under 35 U.S.C. 154(b) by 114 days.

(21) Appl. No.: 12/582,123

(22) Filed: Oct. 20, 2009

(65) Prior Publication Data

US 2011/0091362 A1    Apr. 21, 2011

(51) Int. Cl.
*A61L 2/06* (2006.01)
(52) U.S. Cl. .......... 422/309; 422/32; 422/308; 110/235; 110/257; 110/346
(58) Field of Classification Search .................. 422/309, 422/32, 300, 308; 261/606; 110/235, 257, 110/346
See application file for complete search history.

(56) References Cited

U.S. PATENT DOCUMENTS

| | | | | |
|---|---|---|---|---|
| 3,997,406 | A | * | 12/1976 | Arvanitakis ................ 202/175 |
| 5,027,721 | A | * | 7/1991 | Anderson .................... 110/236 |
| 5,201,473 | A | | 4/1993 | Pollock |
| 5,361,708 | A | | 11/1994 | Barnes |
| 5,689,941 | A | | 11/1997 | Gombos et al. |

* cited by examiner

*Primary Examiner* — Sean E Conley
(74) *Attorney, Agent, or Firm* — Robert A. Jensen; Jensen & Puntigam, P.S.

(57) ABSTRACT

A method and apparatus for eliminating mold spores, pathogens and odor from material like equine bedding. The apparatus includes two or more pairs of augers including blades to control the size of the material and to move it in a zigzag fashion through heat.

11 Claims, 6 Drawing Sheets

Flow Diagram
Not to Scale

Flow Diagram
Not to Scale

Main Processing Unit
Not to Scale

Trough Tray Detail End View

Trough Tray End View

Auger Detail

Flow Diagram

ANIMAL WASTE PROCESSING

TECHNICAL FIELD

This invention relates to a method and apparatus for eradicating pathogens and processing animal waste to the point of safe reuse, and more particularly to a plurality of horizontal screw augers mounted in side troughs located in metal containers. The animal waste and other loose material to be dried is introduced into the top of the container and carried horizontally by the augers in a zigzag path, cascading to the bottom for discharge. During the travel, cutting edges or knives chop waste material and break up lumps. Heat from an external source is introduced to the bottom of the container and travels upwardly, counter-current to the manure, vaporizing moisture and in the manure, killing pathogens and mold spores, as well as removing the noxious odors.

BACKGROUND OF THE INVENTION

This invention relates in general to the processing of animal waste, bedding or manure and recycling it into a reusable byproduct for reuse as animal bedding and/or fuel for biomass burners. More specifically, this invention relates to the processing of equine (horse) waste bedding or manure composed mostly of wood products such as shavings and sawdust and reclaiming the wood products, transforming this into a clean, safe, reusable byproduct to be reused as horse bedding and/or bio-mass burner fuel.

Current practices for equestrian facilities and farms is to daily remove the areas of soiled bedding in the horse's stalls and transport it by wheelbarrow or other means to a storage pile. Replacement bedding is then added to the stall and raked to provide an even sleeping/resident bedding for the animal. The soiled bedding (manure) is allowed to stockpile over a period of time, dependent on the number of horses at the facility until the volume reaches such levels that it requires removing from the farm. Bins or other devices are then utilized to hold the manure, and then it is trucked away to a landfill site or other collection area, where it is dumped. There are very limited uses for this waste product at this stage, and it often becomes a nuisance material, accumulating and causing foul odors, greenhouse gas release and other environmental concerns.

Carbon monoxide and tailpipe emissions from the transporting vehicles are also becoming of more concern with the influx of residential areas now encroaching on what used to be historic farmland. This invention will have the capacity to process much of the manure on the host farm and surrounding farms without the need to truck it, often passing through residential and commercial areas and taking it at often great distances to be stockpiled with little or no residual value.

Description of the Current Equine Manure Disposal Methods

Composting: This is a method of disposal that has some merit, as it reuses the waste for potting soil. With the high cost of land, available sites to perform composting without adversely impacting neighbors is limited. It should always remain an acceptable, however limited, disposal method.

Spreading on Land Option: This practice seems acceptable for blueberry fields and some other crops, but has not yet achieved widespread acceptance and use. Studies of the long-term ramifications of this practice indicate possible dilution of soils by the addition of wood products to the soil.

Landfill Dumping: This method is used only when no other option is available. Transportation and landfill tipping costs are increasing significantly. Many landfills are not accepting manure, as this interferes with the anaerobic decomposition if not applied properly.

Stockpiling: This is the basic practice of many smaller farms because they can't afford storage bins for pickup and don't generate enough manure to make pickup attractive to the haulers. This method is causing the most concern in the agriculture industry because of its adverse effect on aquifers and properties and because it generates odor concerns.

Prior art known to the inventor includes: U.S. Pat. No. 5,201,473 granted to Pollock on Apr. 13, 1993, which discloses a feeder and measuring device in which bulk material is heated and agitated by a plurality of tines mounted upon rods to control material which is loosened and dispensed.

U.S. Pat. No. 5,347,729 granted to Meyer on Sep. 20, 1994 discloses a plurality of auger-like devices mounted within cylindrical shells for drying food and materials.

U.S. Pat. No. 5,361,708 granted to Barnes on Nov. 8, 1994 discloses an apparatus and method for pasteurizing and drying sludge wherein the material to be dried passes through three separate cylinders while being in contact with hot gasses.

U.S. Pat. No. 5,689,941 granted to Gombos et al on Nov. 25, 1997 discloses a high-density combination dry hay and hay silage livestock feed-making apparatus processing crude silage and dried powder into a consumable product which is then packaged.

None of the prior art known to the inventor includes the process of cutting or declodding the input to prevent jams while providing agitation and heat to result in dried, shredded and pathogen-free material.

SUMMARY OF THE INVENTION

Although there have been many devices produced that will dry various materials in one form or another, animal waste, and specifically equine manure, requires more than just drying to transform it into a viable, useful byproduct. This invention will efficiently dry the material to the desired level and in the throughput volumes required to make the process viable. Drying level can be controlled by the time and temperature set by controlling the speed of the augers and the heating unit output. This is done within a small footprint to save space, yet still produce sufficient throughput.

Animals often suffer from diseases, both minor and major, that can be passed on to other animals through contact with other animals or excreted into their stall bedding either through feces or respiratory excretion. In order to prevent the spreading of these pathogens, the infected waste bedding must be subjected to the required time and temperature within a containment apparatus to kill and remove these tiny microbes from the manure. In order to properly contact all areas of the manure where pathogens may be lurking, it is necessary to have a heating system that agitates the manure sufficiently to allow the heat to reach all areas.

Likewise, common mold spores, which are everywhere in nature, are most likely in the "clean" bedding being introduced into the stalls after the soiled bedding is removed. Although not usually evident, if the sawdust/wood shavings have been stored outside or are damp, these mold spores will begin to grow within the pile or in the stalls. Horses like to eat with their heads down and can very easily breathe in these microscopic mold spores, and this can cause respiratory problems for the animal. This invention will eradicate virtually all pathogens and mold spores from the manure during processing to provide the recycled material to be reused as horse bedding.

Waste hay that is deposited onto the bedding in the bottom of horse stalls has a tendency to ball up and plug augers. This invention includes a series of cutting blades or knives attached to one or more levels of augers to cut this hay into manageable particles. Each pair of augers in the tray is designed to rotate towards each other with a solid surface between them to use as a cutting surface, yet still transport the material to the same end. This invention therefore acts as a classifier or sizing device for particles and will reduce any lumps that may be present in the raw material.

Manure has its own significant odors. These odors are obnoxious to residential areas and cause for confrontations. This invention will heat the ammonia found in the waste bedding from urination to such a degree as to separate the nitrogen from the hydrogen in the ammonia atom and in this way eliminate the foul odors. In a similar manner, odors that may be present in the feces deposited in the bedding and removed from the stalls can be dried sufficiently to turn the feces into a fine powder that is captured later in the dust collection system, thus eliminating any odors from this source.

Materials gathered from the exit conveyor of this invention can be easily tested for desired qualities, sent to a storage bin or sent to a pellet mill and/or bagging system. Processed material will now meet the criteria for both equine and other animal bedding and can be packaged and sold as such in either loose or pelleted form. Processed material will now meet the specifications for bio-mass fuel in either loose or pelleted form and can be packaged or sold in bulk to such industries as greenhouse growers for boiler fuel, stove pellets for home and industrial heating systems or a number of other applications.

BEST MODE FOR CARRYING OUT THE INVENTION

Figure 1:
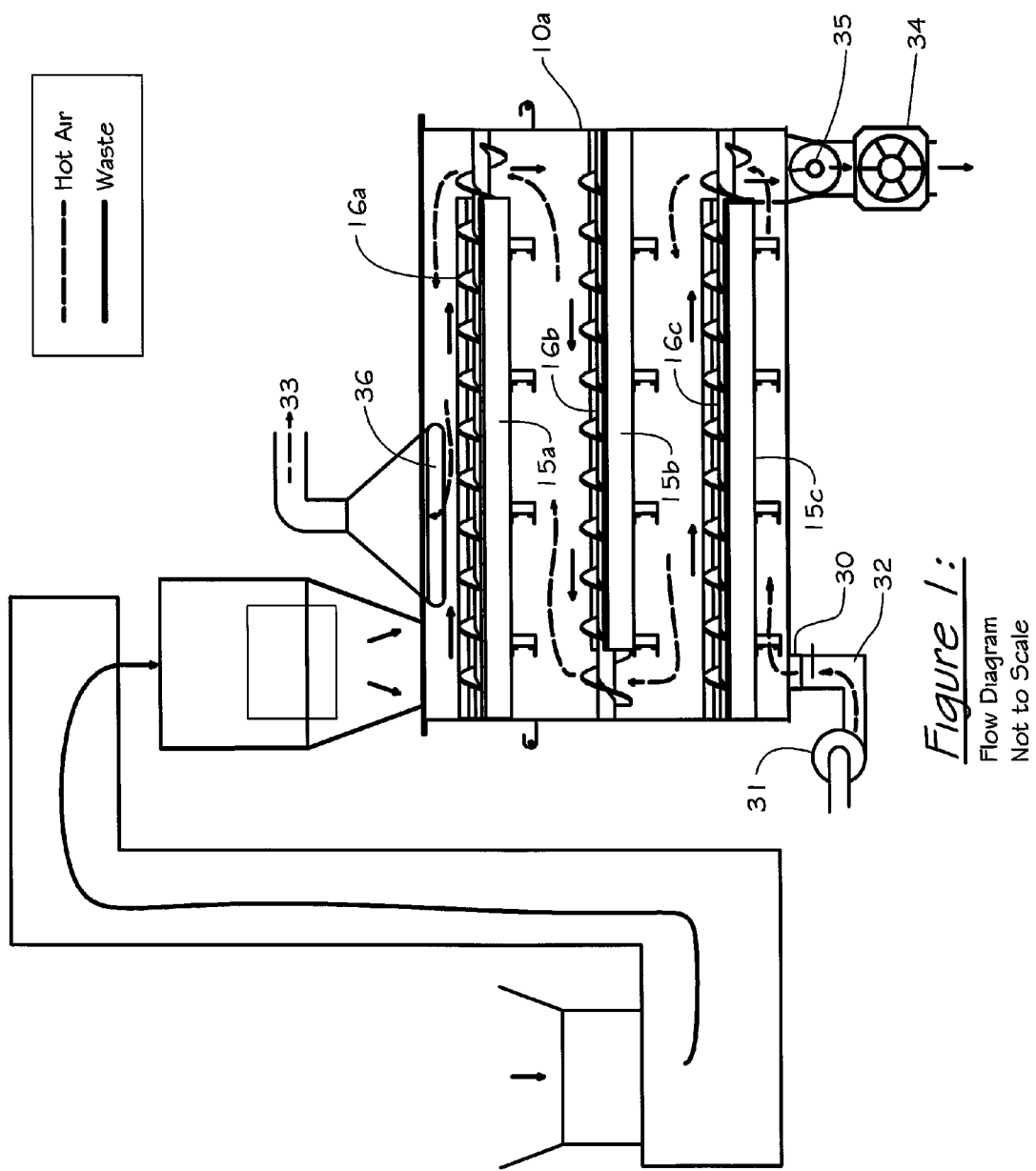
FIG. 1: Flow Diagram of the Animal Waste Processing, Pathogen Eradication and Material Recovery Device from infeed hopper to material exit airlock.
Figures 2, 2A:
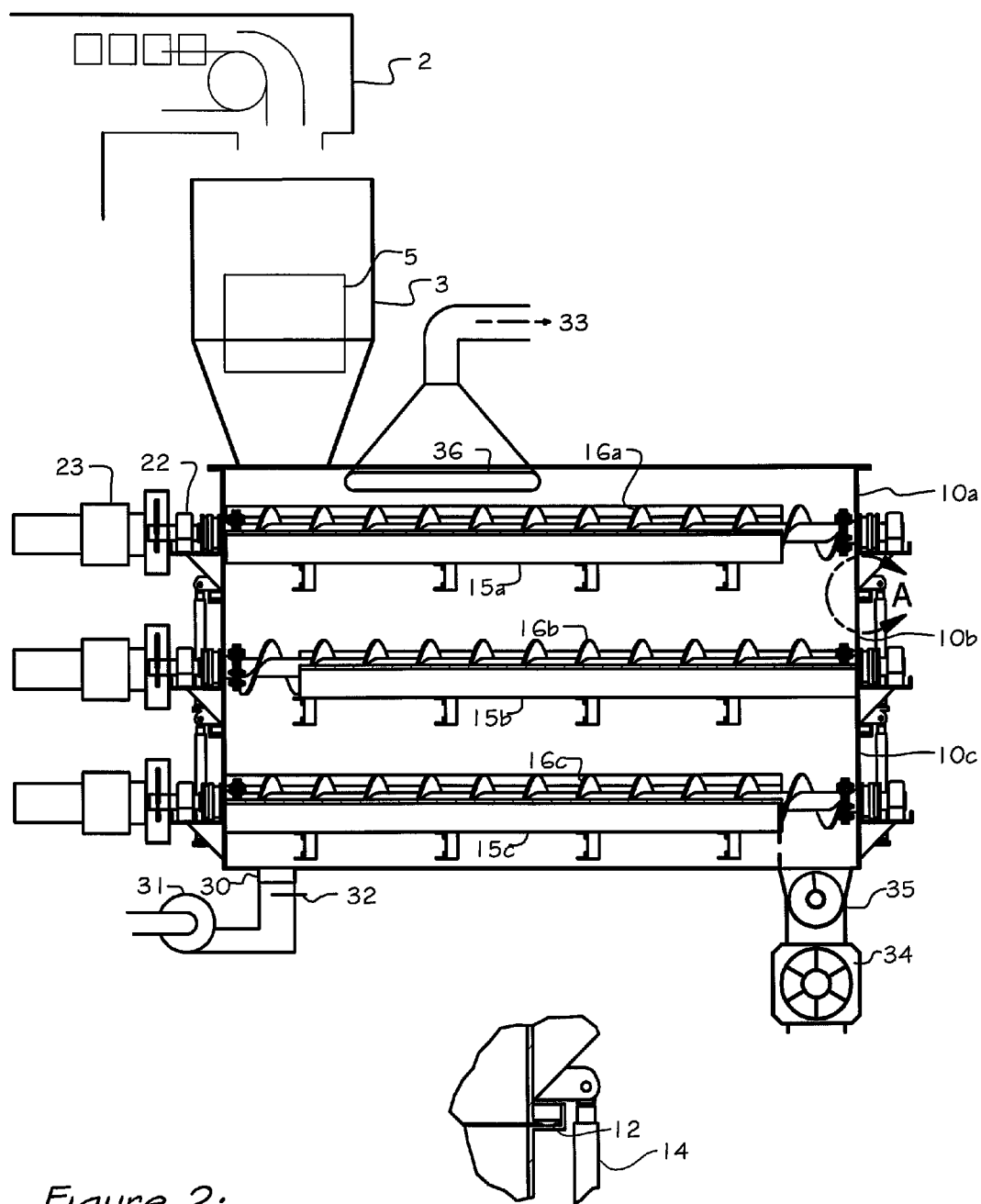
FIG. 2: Main Processing Unit, Device 10: General configuration of the Main Processor of this invention, including the trough trays, screw augers, sections, hydraulic lifting pistons, locking devices, intake hopper c/w distribution arms, bucket elevator, infeed hopper, material discharge airlock, moist air exhaust, hot air intake fan.
Figure 3:
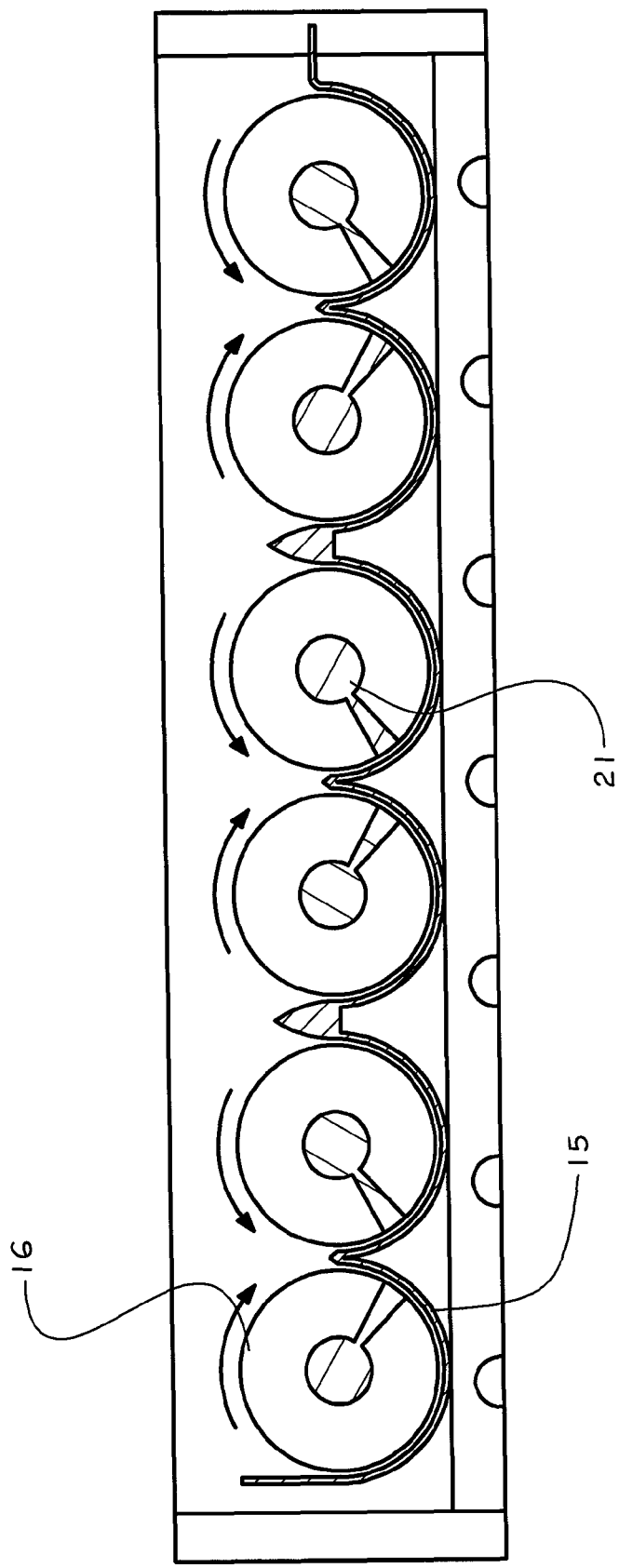
FIG. 3: Trough tray detail with screw augers showing rotation direction.
Figure 4:
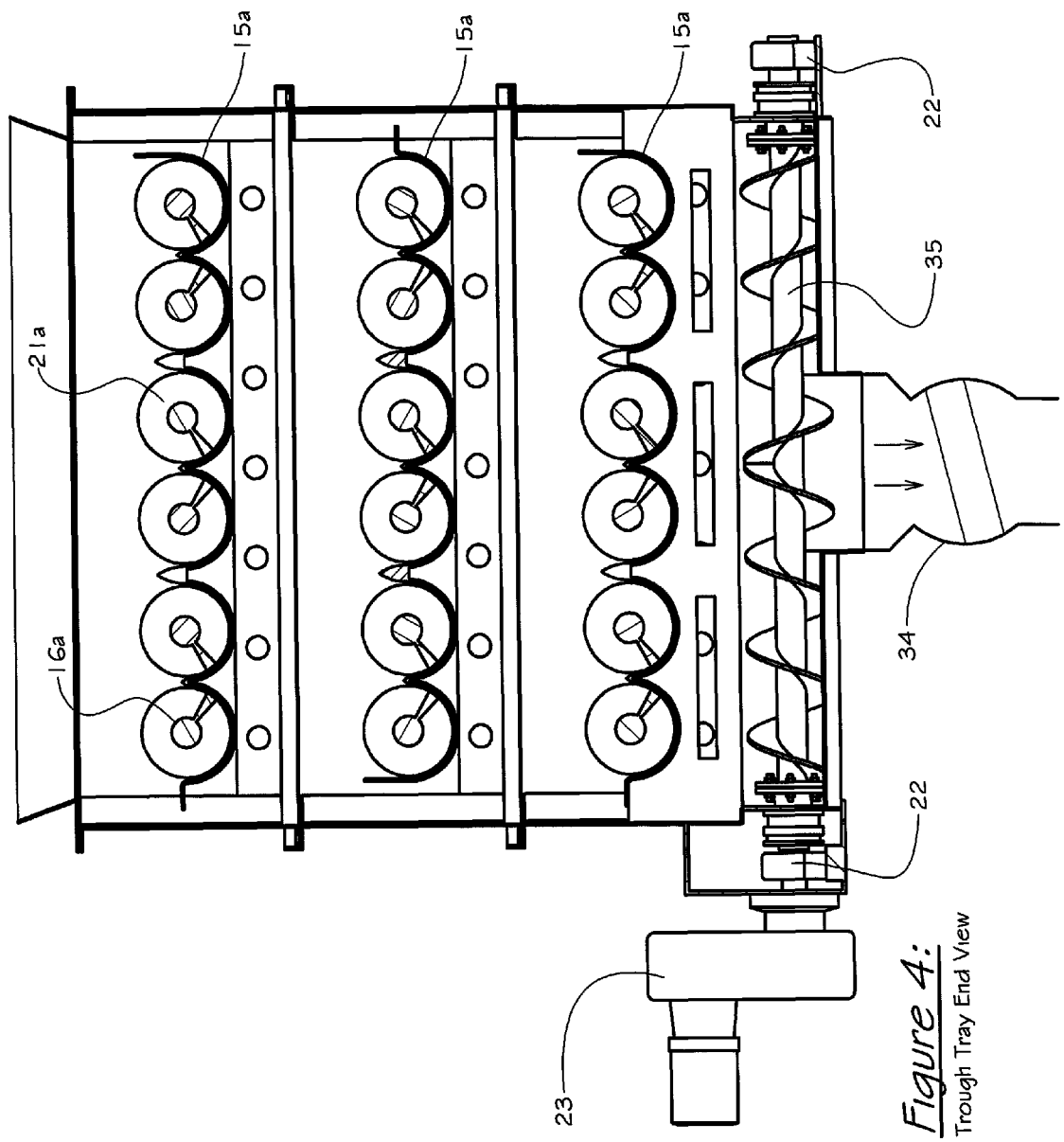
FIG. 4: Trough tray configuration end view.
Figure 5:
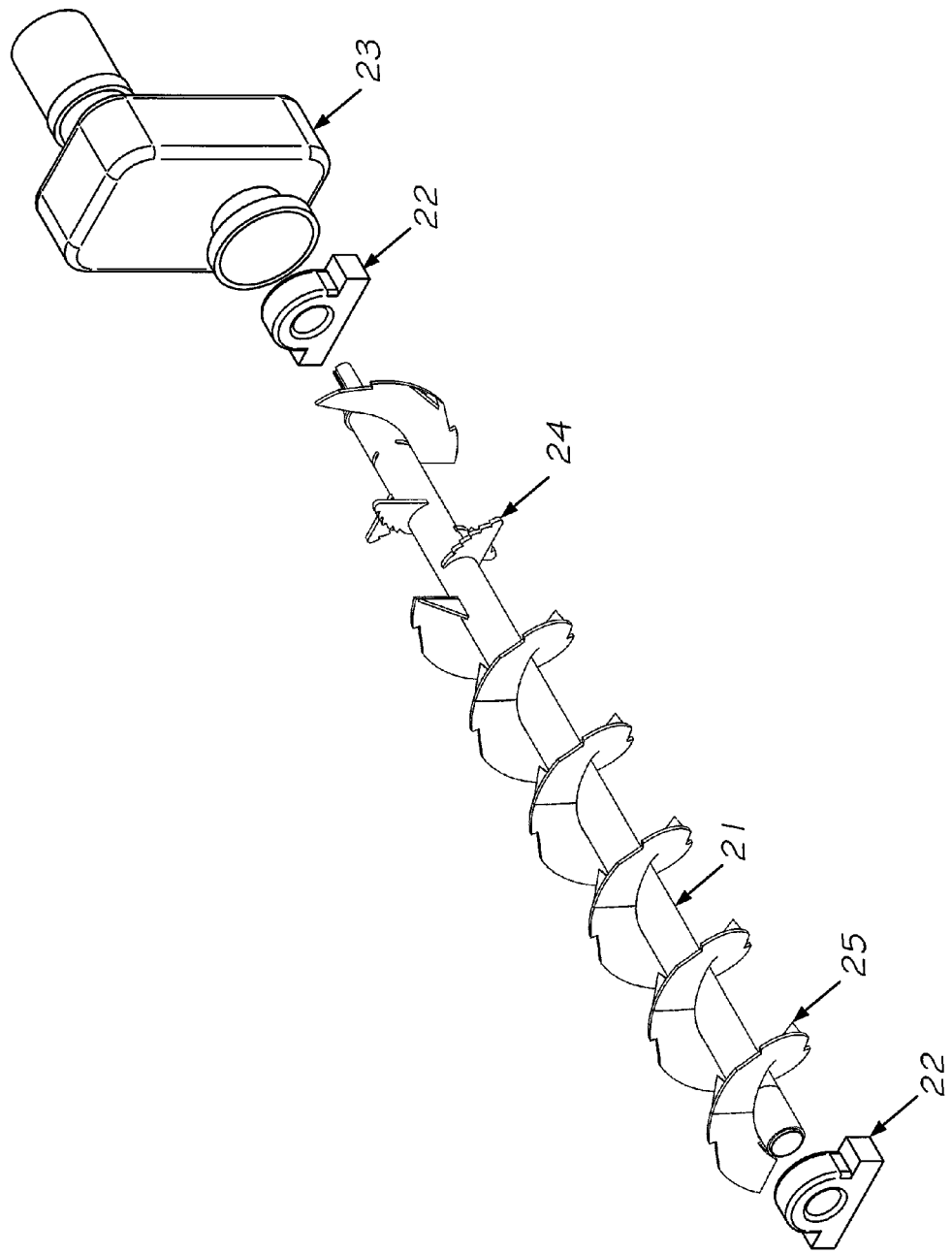
FIG. 5: Screw auger showing blades or knives with bearings and drive.
Figure 6:
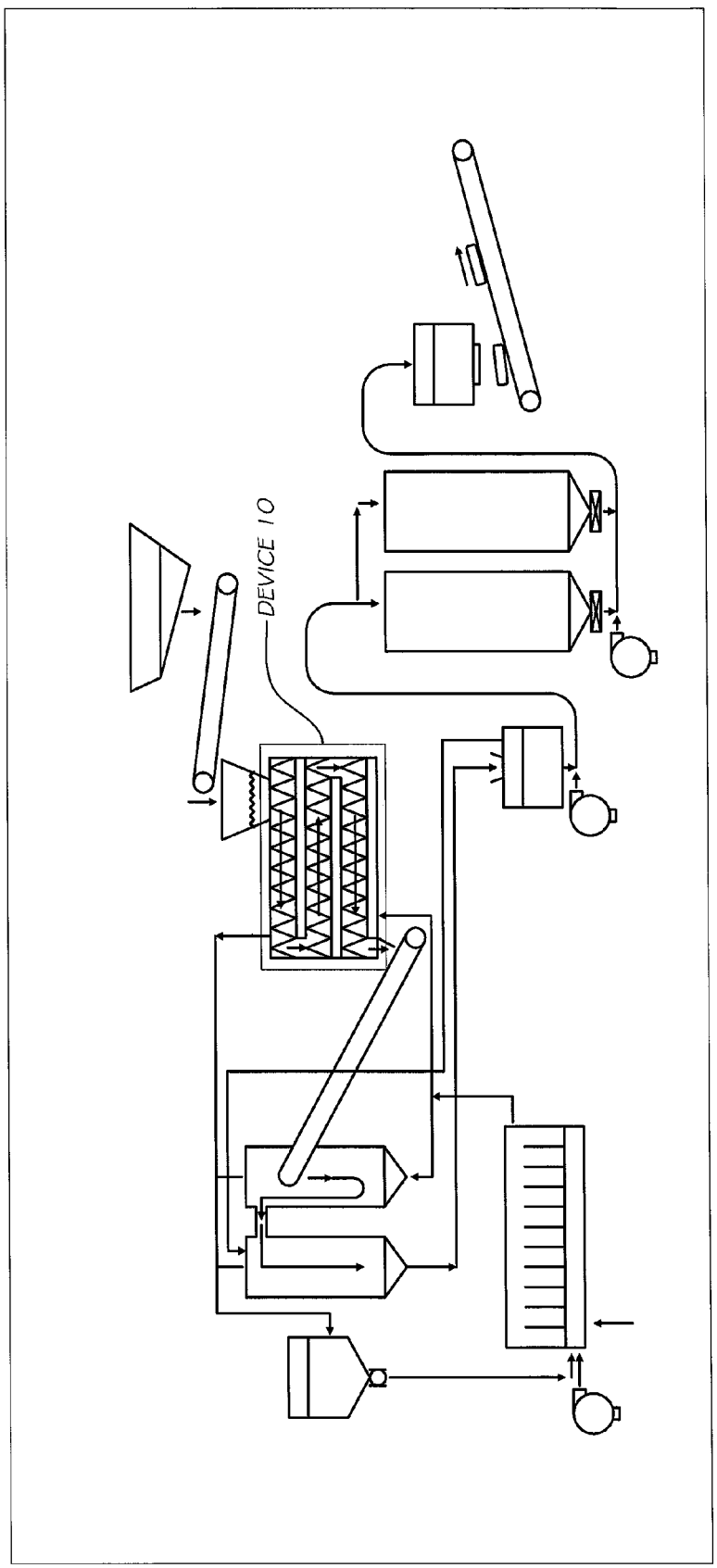
FIG. 6: Flow diagram of how this invention fits into a complete animal waste processing system.

With reference to the drawings, the processing device of this invention is generally designated by the reference number 10. Device 10 includes a base unit 11 that can be mounted with bolts onto a concrete pad that rests upon the floor of a processing plant and supports the various components of device 10.

Device 10 is essentially a rectangular structure that is divided horizontally into one or more separate sections, three (3) sections are shown and indicated by the sub-reference numbers 10*a*, 10*b* and 10*c*. Each section nests into the section below and the area between the sections is sealed with a high temperature sealing gasket, 12. Hydraulic lifting pistons, 14*a*, 14*b*, 14*c* and 14*d*, located at the four corners of device 10 can be electronically operated to lift each of the top two sections (10*a* & 10*b*) either separately or together to provide an opening between the sections for access to the components within.

Inside each section of device 10 is a tray of troughs, 15*a*, 15*b* and 15*c*. These troughs are joined together horizontally and the number of troughs is determined by the number of screw augers, 16, that will be installed in each section. Each tray, generally referred to as 15, is supported from the sides of each section and by stiffeners, 17, that attach to the sides of each section and run below the trays. Trays are cut short of the length of the screw augers to allow for a material drop zone at the appropriate end of each screw auger length and also to allow hot air to travel from section to section.

The screw augers, 16, can be constructed in whatever length and diameter is required for the desired throughput of the device 10, but must be in pairs of two, no less than two in parallel and no more than ten in one section. These screw augers are comprised of a core, 21, that is attached to a bearing, 22, at one end and a driving (turning) device, 23, at the other end. Fins, 24, are attached to the core in a helical pattern that allows for material to be transported from one end of the screw auger to the other. Augers work in pairs in order to project the material towards each other as it passes the length of the auger. In one or more sections, augers will have sharp blades or knives, 25, attached as shown that will cut the loose hay and other long strands and break up any lumps into smaller sizes for ease of movement and for later use. Blades or knives use the narrow gap between the auger fins and the trough as a cutting surface. Blades or knives will require sharpening or replacing from time to time.

Augers are controlled by variable speed devices (23) that can be slowed or increased in speed in tandem with each layer of augers to give the desired speed for optimum processing. The speed of the augers in the troughs increases exponentially from the top layer to the bottom layer.

A material distribution system, 5, is located at the infeed on the top of device 10. This system distributes the incoming manure material evenly from one side of the first level of augers to the other. Distribution arms, 6, move back and forth to accomplish this task. A limit switch, 4, controls the level of manure in the distribution hopper, 3, to prevent overloading of material from the bucket elevator, (not shown). An infeed hopper, (not shown) receives the wet manure as it is loaded by a loading machine, (not shown).

Hot air generated from an external heat source is introduced into the bottom of device 10 through an opening, 30, assisted by an electrically-driven fan, 31. A temperature probe, 32, determines the temperature of this hot air at intake and relays this information back to a control panel, (not shown). A cross screw auger 35 working from each side of bottom tray directs the processed material into the airlock 34. The airlock prevents hot air from leaving the device 10 at the bottom and forces it to travel upward through the device. The control panel automatically sets the incoming hot air temperature to the desired setting by throttling the external heat source either up or down as required, using cool air to reduce temperature and removing cool air to increase temperature. Hot air at the desired temperature travels across the bottom of the lowest auger tray trough, heating it by contact. Heat is then transferred by induction indirectly to the material being transported by the augers in that trough tray. Hot air also travels to the open end at the bottom of the next trough level and penetrates through the dropping material, adding heat as it surrounds the particles, releasing moisture in the material being tumbled and carried by the augers. In the process, heat contacts the underside of the next tray of troughs above and this process is repeated. This process is then repeated for all levels of trays in device 10, with hot air being utilized to heat material both directly and indirectly from tray to tray.

During this process, moisture released from the wet material in each section passes upwards to the top tray where it is captured by the outlet fan, 33, and directed to a moisture separator, (not shown), to remove water if it is desired that the heat be reused in another part of the over all system, or this moist air with fine dust particles it directed to the system dust collection system, (not shown), where the fine dust is captured and removed from the air stream and the moist air exits the system through an exhausting system, (not shown), to atmosphere. Exhausted air emissions meet or exceed all regulatory air emissions requirements.

During the heating process as described above, any pathogens, mold spores or other contaminants are released from the material through the release of the moisture. These contaminants become airborne and can then be destroyed by the hot air. This destruction is based on a "time and temperature" formula as determined by pathogen/contaminant/mold spore eradication tables available from recognized laboratories, universities or regulatory bodies. The system has the capability to regulate the hot air temperatures and control the speed of the material traveling through device 10 to assure compliance with the eradication requirements.

During the heating process and pathogen eradication as described above, the incoming wet manure material is dried to the desired level for either loose animal bedding or for pelletizing into pellets for use as either animal bedding or fuel pellets. The percent of the moisture removed can be controlled in a similar fashion as described above for pathogen eradication.

Processed material that has now passed through the entire processing system exits device 10 through an airlock, 34, located at the drop zone of the bottom auger tray. The airlock prevents hot air from escaping device 10 with the material on exit. Material then enters a conveyor, (not shown), and is conveyed to other processes of the over all system where further drying may take place if required. Test samples can be removed from the test port, 35, and sent to a laboratory for testing.

The throughput of device 10 is determined by several factors: (i) number of sections or levels of augers in device 10, (ii) number of augers/auger troughs in each tray level, (iii) diameter of the augers, (iv) length of the augers, (v) speed of auger rotation during operation, and (vi) desired level of dryness required.

Although a preferred embodiment has been disclosed for purposes of illustration, it should be understood that various changes and modifications and substitutions could be made in the preferred embodiment without departing from the spirit of the invention as defined by the claims which follow:

What is claimed is:

1. A processor for waste organic material, comprising:
    a container having an opening on an upper side to admit said waste organic material and an outlet on a lower side to remove processed waste organic materials from the container;
    a first tray housed in said container to receive said waste organic material from said opening, said first tray comprising a first pair of screw augers to move said waste organic material along said first tray, said first tray terminating short of said first pair of screw augers;
    a second tray housed in said container to receive said waste organic material from said first tray, said second tray comprising a second pair of screw augers to move said waste organic material along said second tray in a different direction of movement than in said first tray, said second tray terminating short of said second pair of screw augers; and
    a source of hot air provided to said container, said hot air traveling along said first and said second trays to heat said waste organic material.

2. The processor as in claim 1, wherein said hot air enters at a bottom of said container, traveling in a direction opposite said waste organic material in said first tray and exits through a top of said container.

3. The processor as in claim 1, wherein said first pair of screw augers are parallel to each other.

4. The processor as in claim 1, wherein said waste organic material moves said in second tray in an opposite direction of movement in said first tray.

5. The processor as in claim 3, including a controller to control the rate of input of said waste organic material.

6. The processor as in claim 3, wherein said hot air provided to said container is heated to a temperature to kill pathogens and mold spores in said waste organic material.

7. The processor as in claim 3, wherein at least one of said augers includes knives or cutting edges to remove lumps from said waste organic material.

8. The processor as in claim 2, wherein said first tray is oriented to be horizontal.

9. The processor as in claim 2, wherein said container comprises:
    a first sub-container for housing said first tray;
    a second sub-container for housing second first tray, said second sub-container mating with said first sub-container; and
    a lifting mechanism to lift said first sub-container from said second sub-container.

10. A device for processing organic material, comprising:
    a substantially closed container including an input opening and an output opening;
    a first tray to receive said organic material from said opening, said first tray comprising a first pair of screw augers to move said waste along said first tray, said first tray terminating short of said first pair of screw augers;
    a second tray to receive said organic material form said first tray, said second tray comprising a second pair of screw augers to move said organic material along said second tray in an opposite direction of movement than in said first tray, said second tray terminating short of said second pair of screw augers; and
    a heat source providing heated air to said container to remove pathogens, mold spores and odors from said organic material.

11. The device as claim in claim 10, wherein the waste organic material is equine bedding.

\* \* \* \* \*